(12) United States Patent
Teucher et al.

(10) Patent No.: US 10,456,532 B2
(45) Date of Patent: Oct. 29, 2019

(54) INJECTION DEVICE

(71) Applicant: Sanofi-Aventis Deutschland GMBH, Frankfurt am Main (DE)

(72) Inventors: Axel Teucher, Frankfurt am Main (DE); Michael Jugl, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 169 days.

(21) Appl. No.: 15/026,430

(22) PCT Filed: Oct. 13, 2014

(86) PCT No.: PCT/EP2014/071911
§ 371 (c)(1),
(2) Date: Mar. 31, 2016

(87) PCT Pub. No.: WO2015/055592
PCT Pub. Date: Apr. 23, 2015

(65) Prior Publication Data
US 2016/0220763 A1  Aug. 4, 2016

(30) Foreign Application Priority Data

Oct. 18, 2013 (EP) .................................... 13189445

(51) Int. Cl.
*A61M 5/32* (2006.01)
*A61M 5/24* (2006.01)

(52) U.S. Cl.
CPC ............ *A61M 5/3202* (2013.01); *A61M 5/24* (2013.01); *A61M 5/2466* (2013.01);
(Continued)

(58) Field of Classification Search
CPC .............. A61M 5/3202; A61M 5/2466; A61M 2005/2474; A61M 2005/247;
(Continued)

(56) References Cited

U.S. PATENT DOCUMENTS

2003/0144633 A1  7/2003  Kirchhofer
2009/0030376 A1  1/2009  Teufelberger et al.
(Continued)

FOREIGN PATENT DOCUMENTS

CN   103269730   8/2013
CN   103328026   9/2013
(Continued)

OTHER PUBLICATIONS

International Search Report and Written Opinion in International Application No. PCT.EP2014/071911, dated Dec. 4, 2014, 10 pages.
(Continued)

*Primary Examiner* — Emily L Schmidt
(74) *Attorney, Agent, or Firm* — Fish & Richardson P.C.

(57) ABSTRACT

Described is an injection device (1) for administering a drug, the injection device (1) comprising a cartridge holder (2) adapted to receive a drug cartridge (3), a hollow injection needle (6) having a proximal tip (6.2) adapted to pierce a septum (4) of the cartridge (3) so as to establish a fluid communication between the cartridge (3) and the needle (6), and a cap (7) arrangeable over the cartridge holder (2) in a manner to cover the needle (6). In an initial state the cartridge (3) is arranged within the cartridge holder (2) with the septum (4) axially spaced from the proximal tip (6.2) of the needle (6). The cap (7) is adapted to move the needle (6) relative to the septum (4) for piercing it on movement of the cap (7) relative to the cartridge holder (2).

7 Claims, 7 Drawing Sheets

(52) U.S. Cl.
CPC .......... *A61M 5/329* (2013.01); *A61M 5/3293* (2013.01); *A61M 2005/247* (2013.01); *A61M 2005/2474* (2013.01); *A61M 2005/2477* (2013.01)

(58) Field of Classification Search
CPC ........ A61M 2005/2477; A61M 5/3204; A61M 5/3213; A61M 5/3271; A61M 2005/3254
See application file for complete search history.

(56) References Cited

U.S. PATENT DOCUMENTS

| | | | |
|---|---|---|---|
| 2012/0041379 A1* | 2/2012 | Macarthur | A61M 5/282 604/192 |
| 2013/0144218 A1 | 6/2013 | Daniel | |

FOREIGN PATENT DOCUMENTS

| | | |
|---|---|---|
| JP | H11-178922 | 7/1999 |
| JP | 2012-529322 | 11/2012 |
| JP | 2013-521858 | 6/2013 |
| JP | 2013-530024 | 7/2013 |
| WO | WO 2010/142813 | 12/2010 |
| WO | WO 2011/112136 | 9/2011 |
| WO | WO2012/003516 | 1/2012 |
| WO | WO 2012/003516 | 1/2012 |
| WO | WO2013/089616 | 6/2013 |

OTHER PUBLICATIONS

International Preliminary Report on Patentability in International Application No. PCT.EP2014/071911, 8 pages.

* cited by examiner

INJECTION DEVICE

CROSS-REFERENCE TO RELATED APPLICATIONS

This application is a U.S. national stage application under 35 USC § 371 of International Application No. PCT/EP2014/071911, filed on Oct. 13, 2014, which claims priority to European Patent Application No. 13189445.3, filed on Oct. 18, 2013, the entire contents of which are incorporated herein by reference.

TECHNICAL FIELD

The invention relates to an injection device for administering a drug.

BACKGROUND OF THE INVENTION

Administering an injection is a process which presents a number of risks and challenges for users and healthcare professionals, both mental and physical. Injection devices typically fall into two categories—manual devices and autoinjectors. In a conventional manual device, manual force is required to drive a medicament through a needle. This is typically done by some form of button/plunger that has to be continuously pressed during the injection. There are numerous disadvantages associated with this approach. For example, if the button/plunger is released prematurely, the injection will stop and may not deliver an intended dose. Further, the force required to push the button/plunger may be too high (e.g., if the user is elderly or a child). And, aligning the injection device, administering the injection and keeping the injection device still during the injection may require dexterity which some patients (e.g., elderly patients, children, arthritic patients, etc.) may not have.

Autoinjector devices aim to make self-injection easier for patients. A conventional autoinjector may provide the force for administering the injection by a spring, and trigger button or other mechanism may be used to activate the injection. Autoinjectors may be single-use or reusable devices.

Usually the injection needle is either integrated with the syringe or has to be attached to a cartridge by the user thus exposing them to a high risk of needle stick injuries.

There remains a need for an improved injection device.

SUMMARY OF THE INVENTION

It is an object of the present invention to provide an improved injection device.

The object is achieved by an injection device according to claim 1.

Exemplary embodiments of the invention are given in the dependent claims.

In an exemplary embodiment, an injection device according to the present invention comprises a cartridge holder adapted to receive a drug cartridge, a hollow injection needle having a proximal tip adapted to pierce a septum of the cartridge so as to establish a fluid communication between the cartridge and the needle, and a cap arrangeable over the cartridge holder in a manner to cover the needle. In an initial state the cartridge is arranged within the cartridge holder with the septum axially spaced from the proximal tip of the needle. The cap is adapted to move the needle relative to the septum for piercing it on movement of the cap relative to the cartridge holder.

In an exemplary embodiment, the cap is adapted to move the needle relative to the septum for piercing it on movement of the cap relative to the cartridge holder in a distal direction or in a proximal direction or on relative rotational movement thereof. The cartridge holder is adapted to allow axial movement of the cartridge within the cartridge holder to and from the needle, which is arranged in the cartridge holder.

In an exemplary embodiment, one or more lateral apertures are arranged in the cartridge holder. The cap comprises one or more internal longitudinal ribs adapted to protrude through the lateral apertures to frictionally clamp and fix the drug cartridge in an axial position within the cartridge holder. Movement of the cap in the distal direction takes along the cartridge until the cartridge hits a stop within the cartridge holder. Continued motion of the cap in the distal direction overcomes friction between the internal longitudinal ribs and the cartridge allowing complete removal of the cap from the cartridge holder.

In an exemplary embodiment, the injection needle is arranged in a needle hub adapted to be moved relative the cartridge holder in which the cartridge is retained and axially fixed. A distal end of the cartridge holder an adapter is provided adapted to telescope with the needle hub. The needle hub and the adapter comprise corresponding snap features for axially coupling the needle hub to the adapter. The snap features are adapted to create an audible and/or tactile feedback on engagement. The cap comprises a needle seat for retaining and positively and/or non-positively fixing the needle hub with respect to relative axial movement and/or relative rotation. A spring is arranged for biasing the cap in the distal direction relative to the cartridge holder. The needle hub and the adapter comprise corresponding first threads for screwing the needle hub onto the adapter. A distal stop is provided in the cap for limiting movement of the needle hub in the distal direction within the cap.

In an exemplary embodiment, corresponding second threads are arranged between the cartridge holder and the cap. The second threads have a handedness which is the opposite of the handedness of the first threads.

As opposed to pre-filled syringes which have a permanently attached needle, the injection device according to the invention store the needle separately from the cartridge prior to use. This may be advantageous when reactions between the drug and the needle should be avoided. Operating the injection device is very simple for the user and does not require additional steps compared with other injection devices having a cap.

Further scope of applicability of the present invention will become apparent from the detailed description given hereinafter. However, it should be understood that the detailed description and specific examples, while indicating exemplary embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

Corresponding parts are marked with the same reference symbols in all figures.

DETAILED DESCRIPTION

Figure 1:
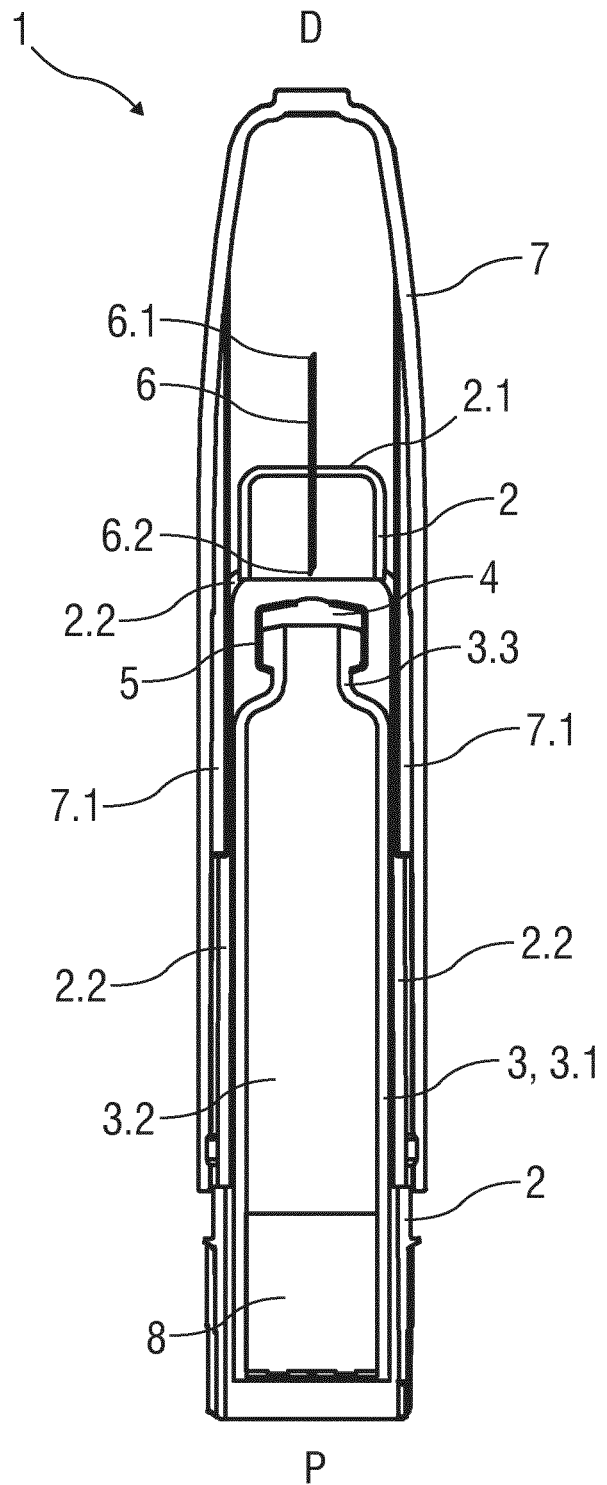
FIG. 1 is a schematic longitudinal section of a first exemplary embodiment of an injection device in an initial state prior to use.

FIG. 1 is a schematic longitudinal section of a first exemplary embodiment of an injection device 1 prior to use. The injection device 1 comprises a cartridge holder 2 adapted to receive a drug cartridge 3. The drug cartridge 3 comprises a body 3.1 defining a cavity 3.2 for receiving a drug. An outlet portion 3.3 having a reduced diameter relative to the body 3.1 is arranged at a distal end of the body 3.1. The outlet portion 3.3 is sealed by a septum 4. In an exemplary embodiment the septum 4 is fixed to the outlet portion 3.3 by a clamp 5. A stopper 8 is arranged within the body 3.1 of the cartridge 3 for proximally sealing the cavity 3.2. The stopper 8 may be axially moved within the body 3.1 to displace the drug from the cartridge 3.

A hollow injection needle 6 having a distal tip 6.1 and a proximal tip 6.2 is arranged in a distal end wall 2.1 of the cartridge holder 2. The distal tip 6.1 is adapted to be inserted into an injection site. The proximal tip 6.2 is adapted to pierce the septum 4 so as to establish a fluid communication between the cavity 3.2 of the cartridge 3 and the needle 6. One or more lateral apertures 2.2 are arranged in the cartridge holder 2. The cartridge holder 2 is adapted to allow axial movement of the cartridge 3 within the cartridge holder 2 to and fro the needle 6.

Furthermore, the injection device 1 comprises a cap 7 arrangeable over the cartridge holder 2 in a manner to cover the needle 6. The cap 7 comprises one or more internal longitudinal ribs 7.1 e.g. corresponding to the number of lateral apertures 2.2 in the cartridge holder 2. The internal longitudinal ribs 7.1 are adapted to protrude through the lateral apertures 2.2 to frictionally clamp and fix the drug cartridge 3 in an axial position within the cartridge holder 2.

In an initial state as illustrated in FIG. 1 the cartridge 3 is arranged within the cartridge holder 2 with the septum 4 axially spaced from the proximal tip 6.2 of the needle 6. The cap 7 is arranged over the cartridge holder 2 with the longitudinal ribs 7.1 protruding through the lateral apertures 2.2 of the cartridge holder 2 clamping and fixing the drug cartridge 3 in its axial position within the cartridge holder 2.

Figure 2:
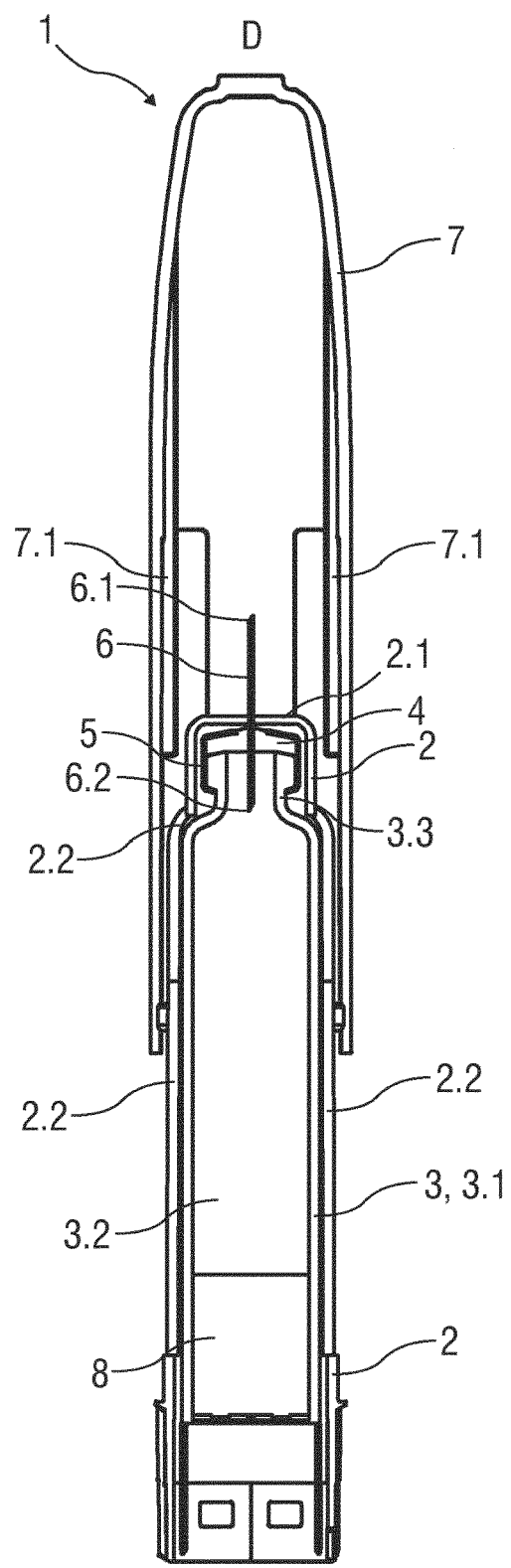
FIG. 2 is a schematic longitudinal section of the injection device being prepared for use.

FIG. 2 is a schematic longitudinal section of the injection device 1 being prepared for use. The cap 7 is being gripped and pulled in a distal direction D relative to the cartridge holder 2 in order to remove the cap 7 from the cartridge holder 2. As the cartridge 3 is clamped to the cap 7 by the internal longitudinal ribs 7.1 protruding through the lateral apertures 2.2 in the cartridge holder 2, the cartridge 3 is being moved along with the cap 7 in the distal direction D relative to the cartridge holder 2 and the needle 6. During this movement the proximal tip 6.2 of the needle 6 pierces the septum 4 thereby establishing a fluid communication between the cavity 3.2 and the needle 6. As the cap 7 is being pulled further taking along the cartridge 3, the cartridge 3 will hit a stop within the cartridge holder 2, e.g. the distal end wall 2.1 or another stop feature 2.3. Continued motion of the cap 7 in the distal direction D overcomes the friction between the internal longitudinal ribs 7.1 and the cartridge 3 allowing complete removal of the cap 7 from the cartridge holder 2. The injection device 1 is now ready to be use.

Figure 3:
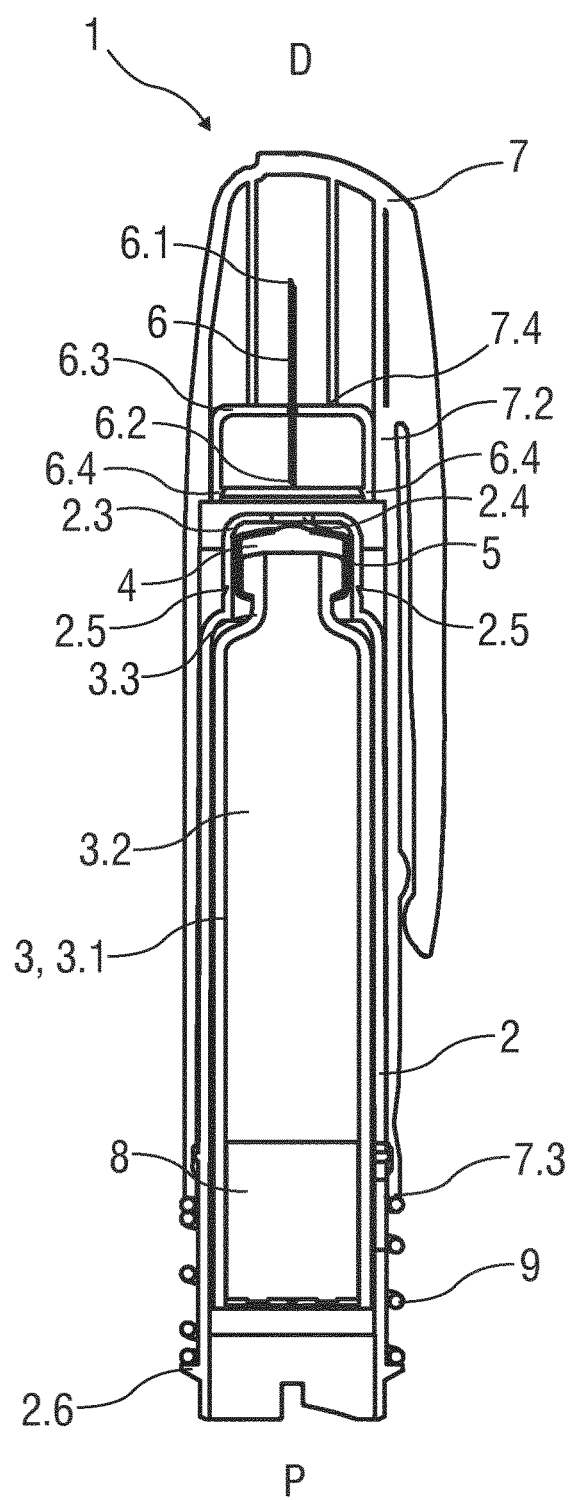
FIG. 3 is a schematic longitudinal section of a second exemplary embodiment of an injection device in an initial state prior to use.

FIG. 3 is a schematic longitudinal section of a second exemplary embodiment of an injection device 1 prior to use. The injection device 1 comprises a cartridge holder 2 adapted to receive a drug cartridge 3. The drug cartridge 3 comprises a body 3.1 defining a cavity 3.2 for receiving a drug. An outlet portion 3.3 having a reduced diameter relative to the body 3.1 is arranged at a distal end of the body 3.1. The outlet portion 3.3 is sealed by a septum 4. In an exemplary embodiment the septum 4 is fixed to the outlet portion 3.3 by a clamp 5. A stopper 8 is arranged within the body 3.1 of the cartridge 3 for proximally sealing the cavity 3.2. The stopper 8 may be axially moved within the body 3.1 to displace the drug from the cartridge 3.

A hollow injection needle 6 having a distal tip 6.1 and a proximal tip 6.2 is arranged in a needle hub 6.3. The distal tip 6.1 is adapted to be inserted into an injection site. The proximal tip 6.2 is adapted to pierce the septum 4 so as to establish a fluid communication between the cavity 3.2 of the cartridge 3 and the needle 6.

The cartridge holder 2 is adapted to retain and axially fix the cartridge 3 within. At a distal end of the cartridge holder 2 an adapter 2.3 having a reduced diameter is provided. The adapter 2.3 comprises a distal orifice 2.4 for allowing the proximal tip 6.2 of the needle 6 to protrude into the cartridge holder 2 and pierce the septum 4. The needle hub 6.3 and the adapter 2.3 comprise corresponding snap features 6.4, 2.5 for axially coupling the needle hub 6.3 to the adapter 2.3.

Furthermore, the injection device 1 comprises a cap 7 arrangeable over the cartridge holder 2 in a manner to cover the needle 6. The cap 7 comprises a needle seat 7.2 for retaining and frictionally fixing the needle hub 6.3 with respect to relative axial movement. A distal stop 7.4 may be provided in the cap 7 for limiting movement of the needle hub 6.3 in the distal direction D within the cap 7. In an exemplary embodiment a spring 9 is arranged between a proximal face 7.3 of the cap 7 and a rib 2.6 on the cartridge holder 2 which may bias them apart.

In an initial state as illustrated in FIG. 3 the needle hub 6.3 is held in the needle seat 7.2 within the cap 7. The cap 7 is arranged over the cartridge holder 2, in which the cartridge 3 is retained. The cartridge holder 2 and hence the cartridge 3 with the septum 4 are axially spaced from the proximal tip 6.2 of the needle 6.

Figure 4:
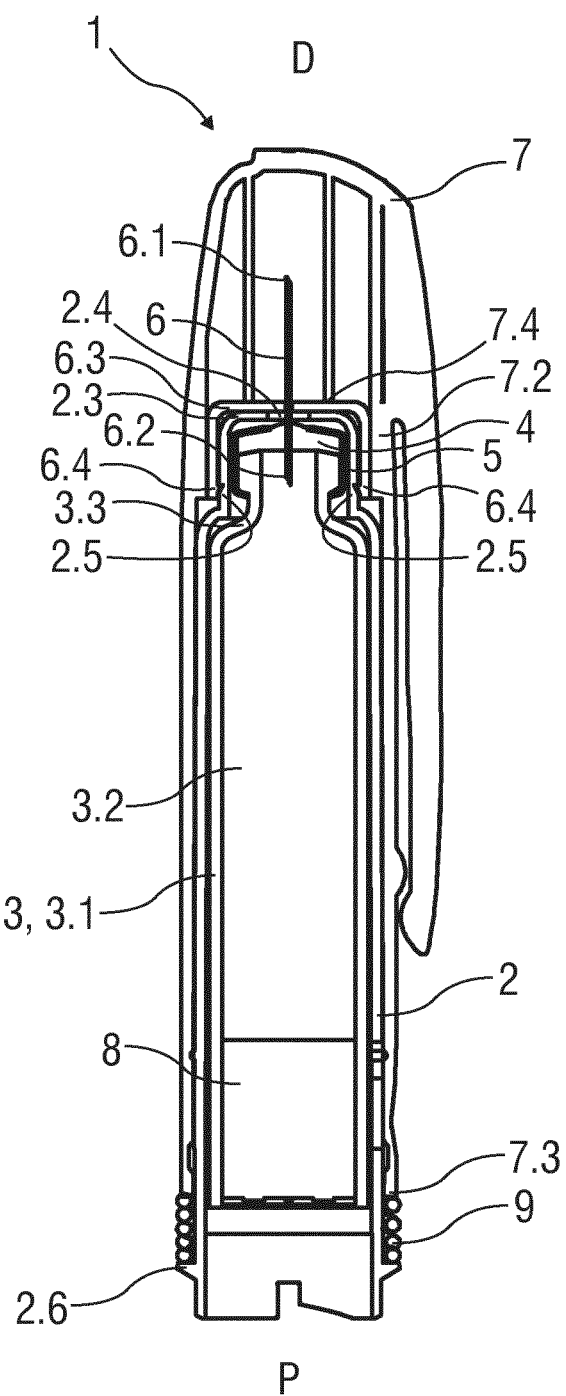
FIG. 4 is a schematic longitudinal section of the injection device being prepared for use.
Figure 5:
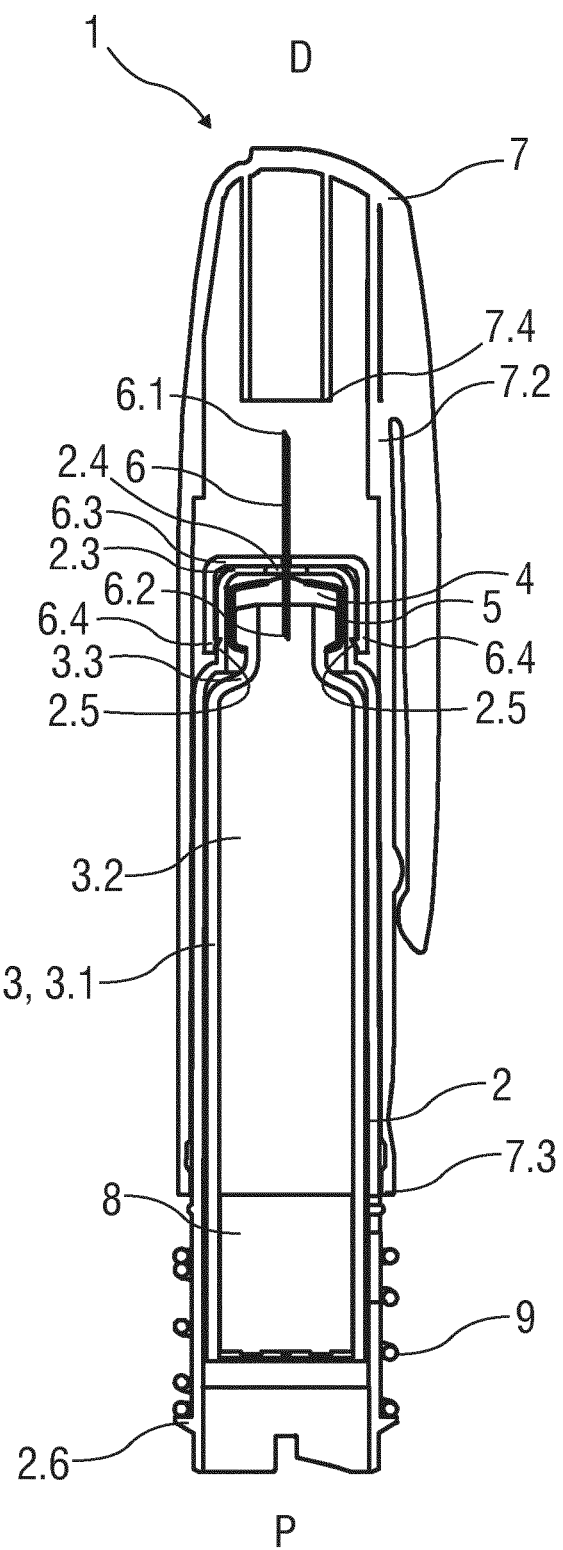
FIG. 5 is a schematic longitudinal section of the injection device ready for use.

FIG. 4 is a schematic longitudinal section of the injection device 1 being prepared for use. The cap 7 is being gripped and pushed in a proximal direction P relative to the cartridge holder 2 thereby also moving the needle 6 towards the cartridge 3 such that the proximal tip 6.2 of the needle 6 pierces the septum 4 thereby establishing a fluid communication between the cavity 3.2 and the needle 6. During this motion the needle hub 6.3 telescopes over the adapter 2.3 until the snap features 2.5, 6.4 engage which may create an audible and/or tactile feedback. Hence, the needle 6 is axially coupled to the cartridge holder 2. Furthermore, during the motion of the cap 7 in the proximal direction P relative to the cartridge holder 2 the spring 9 is compressed. After the audible and/or tactile feedback from the snap features 2.5, 6.4 the cap 7 may be moved in the distal direction D. This movement is supported by the compressed spring 9. As the needle 6 is fixed to the cartridge holder 2 through the snap features 2.5, 6.4 the needle remains engaged to the cartridge holder 2 while the motion of the cap 7 in the distal direction D overcomes the friction between the needle seat 7.2 and the needle hub 6.3 allowing complete removal of the cap 7 from the cartridge holder 2. The injection device 1 is now ready to be used as illustrated in FIG. 5.

In an exemplary embodiment of a slot and pin engagement or another spline feature may be arranged between the cap 7 and the cartridge holder 2 in order to prevent relative rotation.

Figure 6:
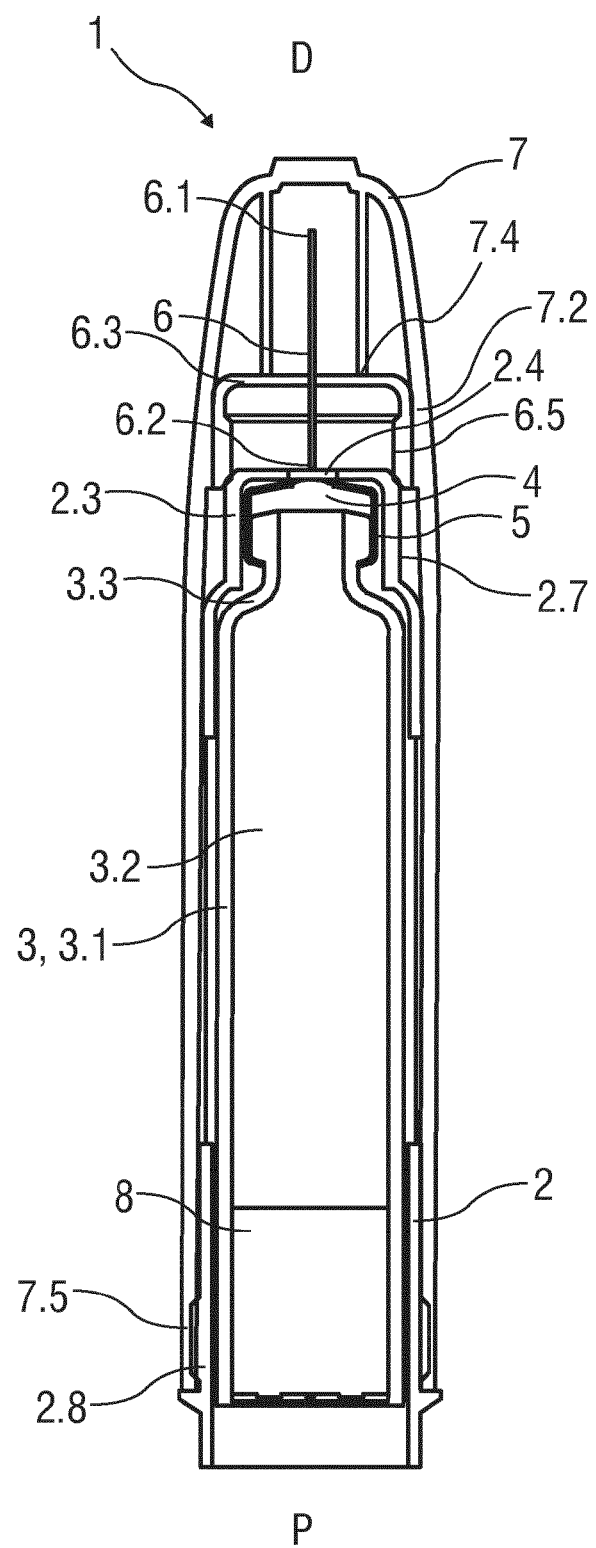
FIG. 6 is a schematic longitudinal section of a third exemplary embodiment of an injection device in an initial state prior to use.

FIG. 6 is a schematic longitudinal section of a third exemplary embodiment of an injection device 1 prior to use. The injection device 1 comprises a cartridge holder 2 adapted to receive a drug cartridge 3. The drug cartridge 3 comprises a body 3.1 defining a cavity 3.2 for receiving a drug. An outlet portion 3.3 having a reduced diameter relative to the body 3.1 is arranged at a distal end of the body 3.1. The outlet portion 3.3 is sealed by a septum 4. In an exemplary embodiment the septum 4 is fixed to the outlet portion 3.3 by a clamp 5. A stopper 8 is arranged within the body 3.1 of the cartridge 3 for proximally sealing the cavity 3.2. The stopper 8 may be axially moved within the body 3.1 to displace the drug from the cartridge 3.

A hollow injection needle 6 having a distal tip 6.1 and a proximal tip 6.2 is arranged in a needle hub 6.3. The distal tip 6.1 is adapted to be inserted into an injection site. The proximal tip 6.2 is adapted to pierce the septum 4 so as to establish a fluid communication between the cavity 3.2 of the cartridge 3 and the needle 6.

The cartridge holder 2 is adapted to retain and axially fix the cartridge 3 within. At a distal end of the cartridge holder 2 an adapter 2.3 having a reduced diameter is provided. The adapter 2.3 comprises a distal orifice 2.4 for allowing the proximal tip 6.2 of the needle 6 to protrude into the cartridge holder 2 and pierce the septum 4. The needle hub 6.3 and the adapter 2.3 comprise corresponding first threads 6.5, 2.7 for screwing the needle hub 6.3 onto the adapter 2.3.

Furthermore, the injection device 1 comprises a cap 7 arrangeable over the cartridge holder 2 in a manner to cover the needle 6. The cap 7 comprises a needle seat 7.2 for retaining and positively or non-positively fixing the needle hub 6.3 with respect to relative rotation. A distal stop 7.4 is provided in the cap 7 for limiting movement of the needle hub 6.3 in the distal direction D within the cap 7. Corresponding second threads 2.8, 7.5 are arranged between the cartridge holder 2 and the cap 7. The second threads 2.8, 7.5 have a handedness which is the opposite of the handedness of the first threads 2.7, 6.5. For example, the first threads 2.7, 6.5 may be right handed while the second threads 2.8, 7.5 are left handed or vice versa.

In an initial state as illustrated in FIG. 6 the needle hub 6.3 is held in the needle seat 7.2 within the cap 7. The cap 7 is arranged over the cartridge holder 2, in which the cartridge 3 is retained. The second threads 2.8, 7.5 are at least almost fully engaged. The first threads 2.7, 6.5 are not or only marginally engaged thus limiting axial movement of the needle 6 in the proximal direction P. The cartridge holder 2 and hence the cartridge 3 with the septum 4 are therefore axially spaced from the proximal tip 6.2 of the needle 6.

Figure 7:
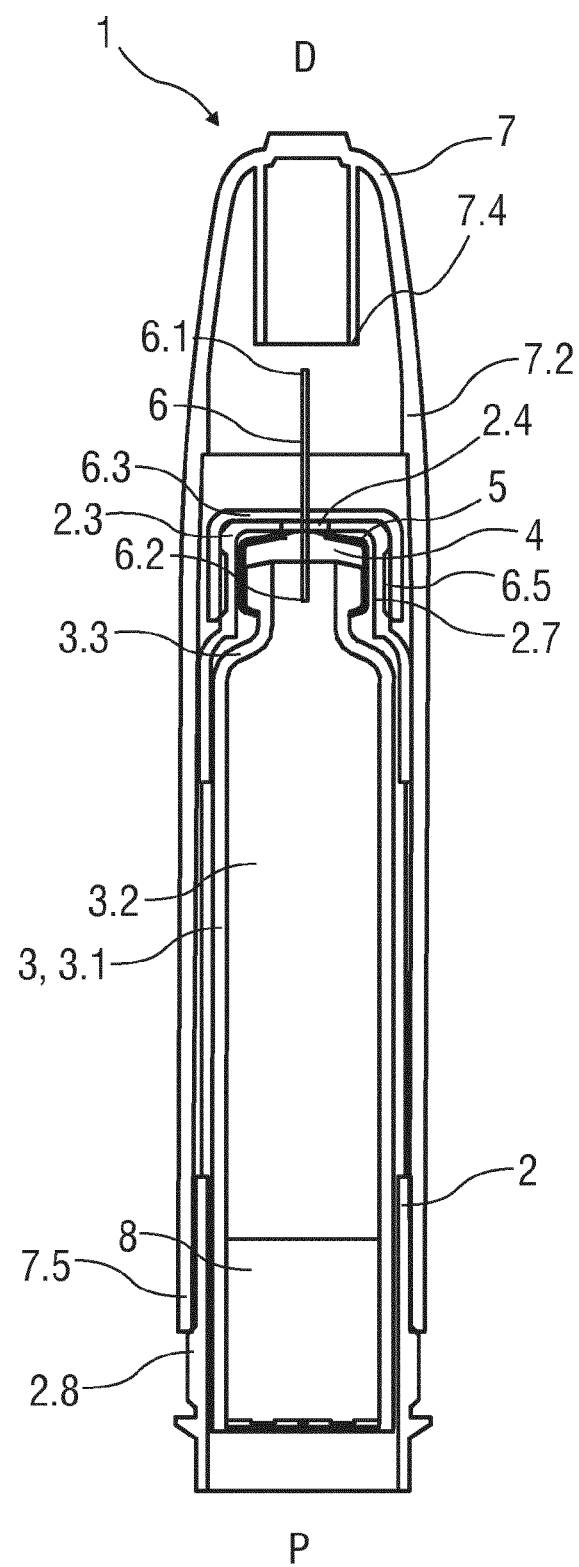
FIG. 7 is a schematic longitudinal section of the injection device being prepared for use.

FIG. 7 is a schematic longitudinal section of the injection device 1 being prepared to be used. The cap 7 is being gripped and rotated in a rotational direction relative to the cartridge holder 2 thereby unscrewing and axially removing the cap 7 from the cartridge holder 2. As the needle 6 is rotationally fixed within the cap 7 this rotation screws the needle hub 6.3 onto the adapter 2.3 of the cartridge holder 2 thereby also moving the needle 6 towards the cartridge 3 such that the proximal tip 6.2 of the needle 6 pierces the septum 4 for establishing a fluid communication between the cavity 3.2 and the needle 6. Hence, the needle 6 is axially coupled to the cartridge holder 2 and the cap 7 may be pulled off. The injection device 1 is now ready to be used.

As opposed to pre-filled syringes which have a permanently attached needle, the injection devices illustrated in FIGS. 1 to 7 store the needle 6 separately from the cartridge 3 prior to use. This may be advantageous when reactions between the drug and the needle 6 should be avoided. Operating the injection device 1 is very simple for the user and does not require additional steps compared with other injection devices having a cap.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl- ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp- Leu-Ser-Lys-Gln-Met-Glu-Glu-Glu-Ala-Val-Arg-Leu-Phe-Ile-Glu-Trp-Leu-Lys-Asn-Gly-Gly-Pro-Ser- Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H-H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Those of skill in the art will understand that modifications (additions and/or removals) of various components of the apparatuses, methods and/or systems and embodiments described herein may be made without departing from the full scope and spirit of the present invention, which encompass such modifications and any and all equivalents thereof.

LIST OF REFERENCES 1 injection device
2 cartridge holder
2.1 distal end wall
2.2 lateral aperture
2.3 adapter
2.4 orifice
2.5 snap feature
2.6 rib
2.7 first thread
2.8 second thread
3 cartridge
3.1 body
3.2 cavity
3.3 outlet portion
4 septum
5 clamp
6 needle
6.1 distal tip
6.2 proximal tip
6.3 needle hub
6.4 snap feature
6.5 first thread
7 cap
7.1 longitudinal rib
7.2 needle seat
7.3 proximal face
7.4 distal stop
7.5 second thread
8 stopper
9 spring
D distal direction
P proximal direction

The invention claimed is:

1. An injection device for administering a drug, the injection device comprising:
a cartridge holder adapted to receive a drug cartridge;
a hollow injection needle having a proximal tip adapted to pierce a septum of the cartridge so as to establish a fluid communication between the cartridge and the needle; and
a cap arrangeable over the cartridge holder in a manner to cover the needle, wherein, in an initial state, the cartridge is arranged within the cartridge holder with the septum axially spaced from the proximal tip of the needle, wherein the cap is adapted to move the needle relative to the septum for piercing the septum on movement of the cap relative to the cartridge holder,
wherein one or more lateral apertures are arranged in the cartridge holder, and the cap comprises one or more internal longitudinal ribs adapted to protrude through the lateral apertures to frictionally clamp and fix the drug cartridge in an axial position within the cartridge holder, and
wherein movement of the cap in a distal direction takes along the cartridge until the cartridge hits a stop within the cartridge holder, wherein continued motion of the cap in the distal direction overcomes friction between the internal longitudinal ribs and the cartridge allowing complete removal of the cap from the cartridge holder.

2. The injection device according to claim 1, wherein the cap is adapted to move the needle relative to the septum for piercing the septum on movement of the cap relative to the cartridge holder in the distal direction or in a proximal direction or on relative rotational movement of the cap relative to the cartridge holder.

3. The injection device according to claim 1, wherein the cartridge holder is adapted to allow axial movement of the cartridge within the cartridge holder to and from the needle, wherein the needle is arranged in the cartridge holder.

4. An injection device for administering a drug, the injection device comprising:
- a cartridge holder adapted to receive a drug cartridge;
- a hollow injection needle having a proximal tip adapted to pierce a septum of the cartridge so as to establish a fluid communication between the cartridge and the needle; and
- a cap arrangeable over the cartridge holder in a manner to cover the needle, wherein, in an initial state, the cartridge is arranged within the cartridge holder with the septum axially spaced from the proximal tip of the needle, wherein the cap is adapted to move the needle relative to the septum for piercing the septum on movement of the cap relative to the cartridge holder, wherein movement of the cap in a distal direction takes along the cartridge until the cartridge hits a stop within the cartridge holder, wherein continued motion of the cap in the distal direction overcomes friction between the cartridge and one or more internal longitudinal ribs of the cap, allowing complete removal of the cap from the cartridge holder.

5. The injection device according to claim 4, wherein the cap is adapted to move the needle relative to the septum for piercing the septum on movement of the cap relative to the cartridge holder in the distal direction or in a proximal direction or on relative rotational movement of the cap relative to the cartridge holder.

6. The injection device according to claim 4, wherein the cartridge holder is adapted to allow axial movement of the cartridge within the cartridge holder to and from the needle, wherein the needle is arranged in the cartridge holder.

7. The injection device according to claim 4, wherein one or more lateral apertures are arranged in the cartridge holder, and the one or more internal longitudinal ribs of the cap are adapted to protrude through the lateral apertures to frictionally clamp and fix the drug cartridge in an axial position within the cartridge holder.

* * * * *